United States Patent
Caps

(10) Patent No.: US 7,400,999 B2
(45) Date of Patent: Jul. 15, 2008

(54) DETERMINATION OF THE GAS PRESSURE IN AN EVACUATED THERMAL INSULATING BOARD (VACUUM PANEL) BY USING A HEAT SINK AND TEST LAYER THAT ARE INTERGRATED THEREIN

(75) Inventor: Roland Caps, Kleinwallstadt (DE)

(73) Assignee: VA-Q-TEC AG, Wurzburg (DE)

( * ) Notice: Subject to any disclaimer, the term of this patent is extended or adjusted under 35 U.S.C. 154(b) by 386 days.

(21) Appl. No.: 10/508,358

(22) PCT Filed: Mar. 11, 2003

(86) PCT No.: PCT/EP03/02482

§ 371 (c)(1),
(2), (4) Date: Feb. 25, 2005

(87) PCT Pub. No.: WO03/085369

PCT Pub. Date: Oct. 16, 2003

(65) Prior Publication Data

US 2005/0199067 A1    Sep. 15, 2005

(30) Foreign Application Priority Data

Apr. 6, 2002   (DE) .............................. 102 15 213

(51) Int. Cl.
*G01K 1/00*   (2006.01)
(52) U.S. Cl. .................................................. 702/130
(58) Field of Classification Search ................. 702/130
See application file for complete search history.

(56) References Cited

U.S. PATENT DOCUMENTS 5,345,814 A * 9/1994 Cur et al. ..................... 73/49.3
5,479,146 A * 12/1995 Herbert ......................... 336/61
5,990,780 A * 11/1999 Caddock, Jr. ................ 338/309
6,935,183 B2 * 8/2005 Ferrario et al. ................ 73/730

FOREIGN PATENT DOCUMENTS

DE        10117021 A    10/2002
JP        62215194 A    9/1987
JP        10239199 A    9/1998

* cited by examiner

*Primary Examiner*—John E Barlow, Jr.
*Assistant Examiner*—Aditya S Bhat
(74) *Attorney, Agent, or Firm*—Frank H. Foster; Kremblas, Foster, Phillips & Pollick

(57) ABSTRACT

The invention relates to the determination of the gas pressure in an evacuated thermal insulating board (9) having an insulating core (1) covered by a film (2). The inventive device comprises an assembly, which is integrated between the insulating core and the covering film of the thermal insulating board and which has a body that acts as a heat sink (3) (Al, Co, Fe, ceramic), and the body's thermal conductivity and thermal capacity relative to volume are greater than those of the insulating core. Said assembly also comprises a test layer (4) (0.3 mm nonwoven fabric made of plastic and glass fibers), which is arranged between the heat sink and the covering film and has a defined thermal conductivity that changes according to the gas pressure inside the evacuated thermal insulating board. From the exterior, a sensor device is applied to or pressed against the test device, which is placed inside the evacuated thermal insulating board and which is covered by the covering film. Said sensor device comprises a body (5) (coppered steel 78° C., thermoelement (6)) having a distinctly different temperature than that of the test device (heat sink) whereby creating a heat flux, which is influenced by the thermal conductivity of the test layer, said thermal conductivity varying according to the gas pressure inside the thermal insulating board, and the magnitude of this heat flux is metrologically determined. The heat sink (3) can be provided in the form of a bottom part of a container for a getter material.

38 Claims, 1 Drawing Sheet

US 7,400,999 B2

DETERMINATION OF THE GAS PRESSURE IN AN EVACUATED THERMAL INSULATING BOARD (VACUUM PANEL) BY USING A HEAT SINK AND TEST LAYER THAT ARE INTERGRATED THEREIN

CROSS-REFERENCES TO RELATED APPLICATIONS

This application is a submission to enter the national stage under 35 U.S.C. 371 for international application number PCT/EP03/02482 having international filing date 11 Mar. 2003, for which priority was based upon patent application 102 15 213.6 having a filing date of 6 Apr. 2002 filed in Germany.

STATEMENT REGARDING FEDERALLY-SPONSORED RESEARCH AND DEVELOPMENT

Not Applicable

REFERENCE TO AN APPENDIX

Not Applicable

BACKGROUND OF THE INVENTION

1. Field of the Invention

The invention relates to a device for performing a thermal measurement method, from which the gas pressure in an evacuated thermal insulating board can be determined where this latter has an insulating core enclosed in a film. Likewise, the invention centers on a method for measuring the gas pressure inside an evacuated thermal insulating board.

2. Description of the Related Art

Evacuated thermal insulation plates or vacuum panels reach a high insulation effect with the smallest insulation thickness. Usually, they consist of an evacuable, porous core material of low thermal conductivity, and of a vacuum sealed covering shell, the latter composed, for example, of a metallized high-barrier synthetic film. For applications that require longer life spans, in building structures for example, an insulating core of microporous silica has been demonstrated to have advantages. For applications demanding shorter periods of use, the insulating core can also be composed of either an open-pored foam consisting of polyurethane and/or polystyrene, or of fiberglass. Because of the extremely small size of their pores, with diameters of less than one half of a micrometer, a vacuum from 1 to 10 mbar in the core materials is sufficient to practically eliminate the thermal conductivity of the air in micro-porous cores. At these pressure levels, a heat conductivity between 0.004 W/(m*K) and 0.005 W/(m*K) is achieved. An increase of gas pressure to 100 mbars allows the heat conductivity to rise only to around 0.008 W/(m*K) whereas the thermal conductivity averages 0.020 W/(m*K) at normal air pressure of 1000 mbar. Because of the larger pore dimensions of open-pored foams or fiberglass materials, gas pressure levels must lie between 0.01 and 1 mbar in order to significantly suppress the heat conductivity of the air.

The performance and efficient function of the vacuum insulation can be determined by the level of thermal conductivity or by the interior gas pressure. A measurement of thermal conductivity at individual vacuum insulating boards is possible with the normal stationary board measuring method. While such methods enjoy a relative precision, lying below 5% in relation to the absolute thermal conductivity, they are nevertheless extremely time consuming. On the other hand, hitherto available non-stationary techniques, which involve impressing a board with a heat or temperature pulse and measuring such values like temperature or heat flow in a time dependent manner, are faster than the stationary techniques, but they tend to be inexact and prone to false results. Moreover, this is because the measured values depend only on the square root of the thermal conductivity of the insulating core.

The performance of a micro-porous vacuum insulating board can be judged most precisely by means of the level of the interior gas pressure. The initial gas pressure of a newly produced vacuum insulating board typically averages between 1 and 5 mbar. When a suitable high barrier film is used, the interior gas pressure should increase at a rate of no more than 0.2 to 2 mbar per year. So calculated, one can expect to arrive at a doubling of the thermal conductivity in micro-porous thermal insulating boards at the earliest in fifty years. Data about gas pressure levels—as the case may be, the rate of increase over time in a built-in state—is significant for assuring the quality of the vacuum insulating board.

The interior gas pressure of the vacuum panel can be controlled by placing the test object in a vacuum chamber and decreasing the pressure until the film rises noticeably from the insulating core. In this case, the interior pressure of the panel becomes just greater than the gas pressure in the vacuum chamber. This method requires a vacuum insulating chamber that is at least the size of the panels. Moreover, the gas pressure of a vacuum insulating board that has been committed or already built into an insulating object can no longer be determined, so other methods must be found for these purposes.

According to the above observations, the problem inducing the present invention is to make it possible to determine the gas pressure in vacuum insulating boards which are already committed and/or already built into insulating objects; with a high precision, if possible. In such a test, the covering may not be damaged. The technical complexity of the measurement should be held as low as possible; in particular, the time required for it should be kept at a minimum. Furthermore, wherever possible every attention must be paid that the production costs of the vacuum panels are not significantly raised.

BRIEF SUMMARY OF THE INVENTION

The solution to this problem is achieved by a measurement apparatus that includes a device, which is installed between the insulating core and the covering shell of the thermal insulating board, and which comprises a body that acts as a heat sink and has a thermal conductivity and a volume-related thermal capacity that are greater than the corresponding values of the insulating core, and which includes a test layer, arranged between the heat sink and the covering film, with a defined thermal conductivity, that changes as a function of the gas pressure in the evacuated thermal insulating board.

The thermal resistance of the test layer or its thermal conductivity, respectively, depends in a characteristic manner on the gas pressure in the interior of the panel. For fleeces made from fiberglass, with fiber diameters of around 10 µm, the typical gas pressure, where approximately half of the thermal conductivity of settled air at normal pressure will be achieved, amounts to around 2 mbar. With a variation of the gas pressure at or below this pressure level, the thermal resistance of the middle layer will most clearly change. If, on the contrary, the heat conductivity of an insulating core composed, for example of micro-porous silica, is measured, then a clear change of thermal conductivity would be recognizable only at a gas pressure of more than 10 mbar. From the relationship between, on the one hand, the average temperature difference between the heat sink and the sensor component, and on the other, the observed heat flow during the measurement, the thermal resistance of the test layer can be calculated. Knowledge of the thickness of the test layer then yields its thermal conductivity. With the knowledge of the dependence of the test layer's thermal conductivity on the gas pressure in the vacuum panel, the gas pressure in the vacuum panel can be determined. It is, however, also possible to place the measured thermal resistance directly into relation with the inner gas pressure with the help of a calibration measurement, where a known gas pressure is already given.

Likewise for large-pored core materials, such as open-pored polyurethane foam or fiberglass, the methods indicated by the invention can be utilized. Here, the thermal conductivity of a large pored material situated in the test layer—measured by the procedure according to the present invention—varies in a similar manner as the thermal conductivity of the large-pored material which is used as the insulating core in the vacuum panel. Thereby, an elevation of the thermal conductivity of the core material by 20% relative to the entirely evacuated state, resulting from an insufficiently low gas pressure, can be determined.

Thereby, the thermal resistance of the test layer can be measured, for example in such a way that a temperature jump is impressed from outside, and the heat flow over the test layer to the heat sink located behind the test layer is determined. It should, however, also be noted that a measurement is also possible at a reversed heat flow, for example by an initial warming of the body that lies behind the test layer, and by subsequent attachment of a cooler sensor body onto the respective place of the envelope of the thermal insulating board, so that a heat flow from inside to out emerges. A sensor temperature reduced relative to the interior body, can also be realized by cooling the sensor body before the measurement, for example with ice. Although in this method, the body behind the test layer—denoted above as heat sink—now acts as a heat source, and the sensor body attached from outside functions as a heat sink, this method is however more time consuming than the procedure already described with a heat flow from outside to inside, and therefore, the body lying behind the test layer shall henceforth be identified as a heat sink, without loss of generality.

As equipping a vacuum panel with an interior heat sink is not costly, the vacuum panels can be outfitted, in a standard manner, with such a heat sink. In this way, the rapid "In-line-check" of gas pressure after production of vacuum panels is possible.

It has proven advantageous when the thermal conductivity of the heat sink lies above 1 W/(m*k), preferably with thermal conductivity above 2 W/(m*k), and in particular above 10 W/(m*k). In this way the heat absorbed by the heat sink is quickly and evenly spread throughout the entire body, and a measurement-threatening heat accumulation beneath the test layer cannot emerge.

A favorable arrangement results if the thermal conductivity of the heat sink is more than 10 times as great as the thermal conductivity of the test layer is at a gas pressure of less than 100 mbar; preferably, it should be more than 20 times as great, and in particular more than 50 times as great. Owing to the relatively small thermal conductivity of the test layer, nearly ideal heat flow conditions result that allow optimal analysis.

Within the scope of the invention, at or below atmospheric gas pressure, the thermal conductivity of the test layer lies below 1 W/(m*k), preferably below 0.1 W/(m*k), and especially below 0.05 W/(m*k). Preferably, the thermal conductivity of the test layer decreases with sinking gas pressure: for every reduction of gas pressure by one tenth, for example, by 10-75%, respectively, preferably by 20-50%, respectively. In this way, the heat resistance at the pressure level concerned is even more substantially elevated, and allows more exact measurements as a result of the slower temperature changes of the heat sink.

A possibility for realizing the gas pressure dependence of the thermal conductivity of the test layer consists in producing that from an open-pored material. The test layer should feature, however, the highest possible homogeneity of qualities so that reliable measurement values result.

The pore size of the open-pored test layer can be substantially larger than that of the insulating core, such that the thermal conductivity of the gas in the test layer is manifest already at substantially lower gas pressures. In order to be able to measure a lower gas pressure level, a material with coarser structures should be used as test layer to the covering film. With fiber-like materials or fiber matting, (fiberglass for example), the range of detectable levels of gas pressure can be shifted to either higher or lower pressure levels by selection of smaller or larger fiber diameters.

It is within the scope of the invention that the test layer may consist of any of the following: a polypropylene or polyester fiber fleece, a micro fiberglass paper, a fiberglass fleece, a thin layer of open-pored foam material, a layer of aerogel, of diatomaceous earth or of another compressed fine powder. According to the invention, fiber mats or fabrics of glass or synthetic materials, with fiber diameters in the range of from 0.1 to 20 um, show the best characteristics. In principle, however, other materials such as open-pored synthetic foams, fine powders like diatomaceous earth, or layers of aerogel are also possible as test layers.

With respect to thermal measurement, relatively large heat flows, that are good for measurement purposes, result if the thickness of the test layer is nearly uniform, and lies somewhere in the range from 0.05 to 2.0 mm; preferably, it should be more than 0.08 mm, and still better more than 0.1 as well as less than 1 mm, and in particular it should be less than 0.5 mm.

According to the invention, the volume-related thermal capacity C of the heat sink lies between 0.5 J/(cm$^3$*K) and 5.0 J/(cm$^3$*K), preferably between 1.0 J/(cm$^3$*K) and 4.0 J/(cm$^3$*K). In such cases, the sufficient period of heat flow required for exact measurement can be realized with a space-saving test apparatus.

For the heat sink, metals such as aluminum, copper and iron, or a heat conductive ceramic or graphite recommend themselves.

To raise the precision of measurement, the heat sink can be implemented as a flat body with its base surface parallel to the envelope or test layer. In this way, the thickness of such a flat heat sink can be kept uniform. It should lie somewhere between 0.1 mm and 5 mm, preferably at more than 0.2 mm, and especially at more than 0.4 mm, as well as preferably less than 3 mm and especially at less than 2 mm.

The contour of the heat sink can be either round or polygonal, especially square or rectangular, whereby the diameter or the edge length, respectively, amounts to between 5 mm and 100 mm, preferably between 10 mm and 60 mm, and especially somewhere around 30 mm.

The heat sink can be situated on either the top or the underside of the vacuum insulating board, but also at its side edges. In principle, edges or corners of the vacuum insulating board are also suitable, but require a more complex configuration.

If relatively large-pored foams or fiberglass materials are used as the insulating core, there exists the possibility of using the bottom of the inserted getter material holder as a heat sink. For measurements within a lower gas pressure range, a material with a coarser structure can be used as a test layer, a fleece of fiberglass with a fiber diameter of 10 µm, for example.

The procedure according to the invention for determining the gas pressure in a film covered, evacuated thermal insulating board is characterized in that a sensor device is placed on the outside of a device situated inside the evacuated thermal insulating board and covered by a film shell as described above, and in that a temperature jump is created at the covering film. This can be achieved by pressing a body with a substantial temperature difference relative to the device according to the invention thereon. In this way, a heat flow will be created that is dependent on the thermal conductivity of the test layer, which in turn is influenced by the gas pressure within the interior of the thermal insulating board. The value of this heat flow can be determined by measurement techniques, or can be determined and acquired indirectly by other technically measured quantities.

A simple procedure for measuring the temperature on the surface and the heat flow to the heat sink at the same time consists in attaching a thermally conductive sensor body with a temperature difference relative to the interior heat sink, and which carries a temperature sensing device, to the surface of the vacuum panel. Here, it is preferred that the temperature of the sensor body is greater than that in the heat sink within the thermal insulating core. After the sensor apparatus is attached, its heat is transferred off to the interior heat sink, and in this way the temperature of the adjacent part of the sensor apparatus decreases over time. Because of the low thermal capacity of the covering film and the thin test layer, quickly (within approximately 1 to 3 seconds) a thermal equilibrium is reached: if the impressed temperature and the temperature of the interior heat sink change only slightly over time with regard to the temperature difference, then one can assume quasi-stationary conditions. In general, the measurement of time indexed temperature characteristics can then be stopped, if the temperature of the sensor component or of the heat source or the heat sink, respectively, has changed by approximately 2 to 20% of the original temperature difference, preferably by 5 to 10%. Typical measurement intervals lie in the range of 5 seconds to 30 seconds. From the specific thermal capacity of the material of the adjacent sensor component and its dimensions, as well as the temperature change per time unit, the heat flow can be calculated. Then, the thermal resistance of the test layer is proportional to the ratio of the difference between the temperature of the heat sink and that of the sensor apparatus attached from outside on the one hand, and the measured heat flow on the other hand. Before initiating the measurement, the interior heat sink should be in thermal equilibrium with the insulating core. Its temperature is determined before commencing measurement with, for example, a surface temperature probe. The temperature of the sensor component can be regulated to the initial value via an electric heating with an applied thin heating sheet. At the beginning of the measurement, the power supply has to be switched off. Another possibility is to bring the measurement board to the initial temperature by placing it into contact with a heated object.

Preferably, the sensor body comprises a frontal contact surface, whose curvature corresponds approximately to the curvature of the test layer beneath the covering film.

The sensor body can be designed as a cuboid, a prism, or as a (flat) cylinder or as a round disk, respectively, or as another flat body.

The thickness of such a flat body should lie between 0.2 and 100 mm, preferably above 0.5 mm, particularly at more than 1 mm, and on the other hand, below 10 mm, and still better at less than 5 mm.

With respect to the invention, it is recommended to choose the base area of the sensor body such that is either smaller or equal to the surface area of the heat sink, that is, the diameter of the sensor body should not be larger than that of the heat sink. In this way, unnecessary secondary effects can be avoided that could potentially result in false measurements.

The thermal conductivity of the sensor body can correspond approximately with the thermal conductivity of the heat sink situated within the interior of the thermal insulating board. Preferably, the material of the sensor body is a thermally conductive metal like copper, silver, aluminum or iron or steel, respectively.

Furthermore, the invention is characterized by a temperature sensor that is fixed to the sensor body, especially to its surface, or within the volume of the sensor body. As a temperature sensor, for example, a thermo element can be used that influences the thermal capacity of the sensor component only at a minimum.

A further possibility for measuring the heat flow of the sensor component consists in furnishing the sensor body with a regulated electric heat source, for example with a thermal resistor or a thermal film, in order to maintain a nominal temperature. Through this regulator, the temperature of the sensor component will be kept at a constant value, and the power output by the regulator to the sensor component during the measuring procedure can be observed. After a short adjustment period, a quasi-stationary heat flow will likewise emerge as power delivered to the sensor component.

It is also possible to use a heat film with a temperature sensor as a sensor body. At the beginning of the measurement, the heating will be switched on, and via a regulation, a constant and raised temperature is adjusted, and the power necessary therefor is measured. The heating foil can be permanently mounted on the covering film above the heat sink.

The invention may be further improved in that the sensor body is enclosed at the rear and/or at the lateral sides by a thermal insulating material. In order to reduce the heat loss of the sensor body to its surroundings, which can potentially result in a false reading, the body is enclosed—with the exception of its contact surface—in a heat insulation such as a foam material.

Finally, it is in accordance with the teaching of the invention that, during the measurement, the sensor body is enclosed in a can-like or ring- or disc-shaped metallic enclosure that is kept at around the same initial temperature as the sensor body. A temperature regulated heating foil may serve as a covering enclosure. This latter protective shield heated to the same temperature as the sensor body can largely suppress heat outflow from the sensor body to the surroundings or laterally through the covering film.

An alternative method for the determination of the heat flow consists in attaching a heat flow meter to the contact surface of the sensor body. In order to hold it at a constant temperature, the sensor body is preferably coupled to an electrically regulated heat source, or heat sink, such as a heating foil. Then, from the measured thermal flux density and the temperature difference between the heat sink and the sensor body, the thermal resistance of the test layer can likewise be inferred. The heat flow meter should have the lowest possible thermal resistance relative to the ventilated test layer, to a maximum of 10 to 20% of the same.

Further features, details, advantages and effects, with respect to the invention will be apparent from the following description of a preferred embodiment of the invention as well as from the drawing. Hereby:

DETAILED DESCRIPTION OF THE INVENTION

Figure 1:
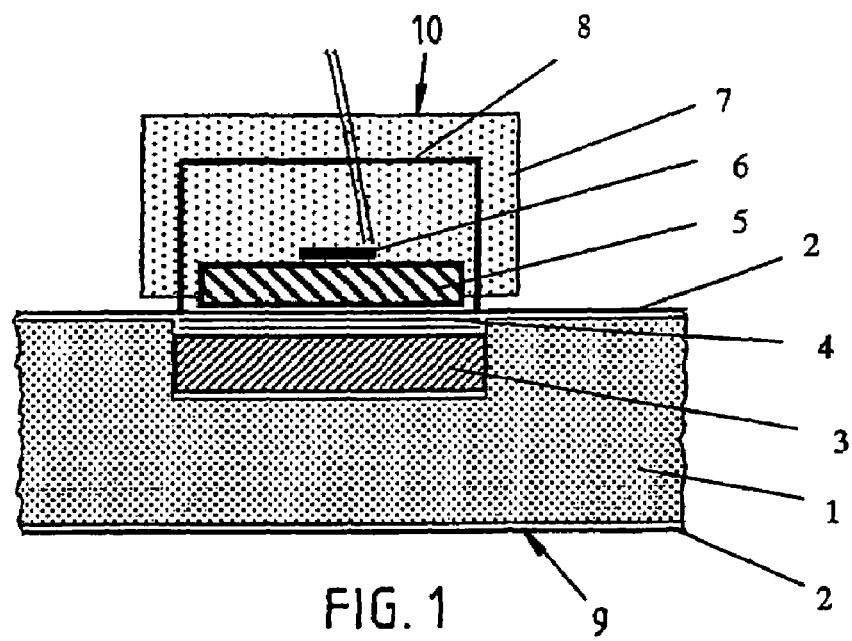
FIG. 1 is a cross section through an evacuated thermal insulating board accommodating a measuring and test apparatus according to the present invention, as well as a sensor device situated above.

The thermal insulating board 9 from FIG. 1 consists of an insulating core 1, which is enclosed on all sides by a foil 2. In accordance with the invention, a small metal or ceramic plate 3, for example made from aluminum, is inserted during the production between the insulating core and the covering foil, and serves as a heat sink. This plate 3 can have a round, square or rectangular shape with a diameter or side length of 30 mm, for example, and a thickness of 2 mm, for example.

According to the invention, a test layer in the form of a thin porous intermediate layer 4 is placed as thermal resistance between the heat sink 3 and the covering foil 2. The pore size of the open-pored test layer 4 can be significantly larger than that of the insulating core 1, so that the gas thermal conductivity in the test layer 4 is noticeable at significantly lower gas pressures than in the insulating core 1. A thickness of only around 0.1 mm to 0.3 mm is indicated for the test layer 4. Therefrom, relatively large heat flows result for the thermal measurement, which are convenient to measure. Despite its limited thickness, the test layer 4 should be as homogenous as possible, but also open pored. In accordance with the invention, fiber fleeces made from synthetic material or fiberglass with very small fiber diameters from around 0.1 μm to 20 μm show the best characteristics. In principle, however, other materials such as open-pored synthetic foams, fine silica powder, or aerogel layers are also suitable as intermediate layers.

After the heat sink 3 is covered by a layer of fiberglass fleece and is inserted into a small recess between the insulating core and the covering foil, such that the test layer 4 faces outward and lies close to the inner side of the covering foil 2, the insulating core 1 is evacuated to a gas pressure of 1 mbar, and the covering foil 2 made from synthetic material is sealed vacuum-tightly.

For the sensor 10, a disc or plate 5 of copper plated steel with a thickness of 1.7 mm and a diameter of 19 mm is used, and to its rear side a thermal element of Type J, serving as a temperature probe/gauge, 6 is soldered. Furthermore, at the rear side, a round piece of foam material with a thickness of 20 mm and a diameter of 20 mm is adhesively affixed as a thermal insulation 7. Additionally, a protective ring 8 heated to the same initial temperature can largely suppress thermal outflow from the sensor board 5 into the surroundings or laterally through the covering foil.

The temperatures of the thermal element 6 are taken with a measurement device at a rate of two measurements per second and are recorded by a computer.

Before the beginning of the measurement, the heat sink 3 is in thermal equilibrium with the surrounding temperature of approximately 20° C. The sensor board 5 is warmed to a temperature of 70° C. The measurement is started when the sensor 10 is pressed onto the measurement area of the insulating board 9. After approximately 20 seconds the measurement is stopped, and the sensor 10 is removed from the measurement area. The measurement is then repeated with another test piece that is evacuated to a gas pressure of only 10 mbar.

Figure 2:
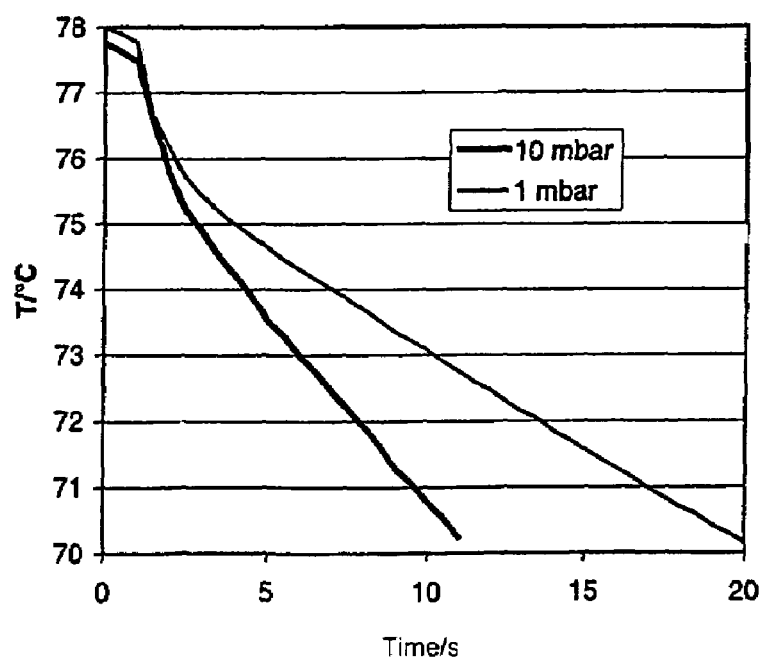
FIG. 2 is a graphic representation of temperature over time as measured by the sensor device in FIG. 1, at different gas pressures within the thermal insulating board.

The measured variations in the temperature course of the sensor board are illustrated in FIG. 2. One discovers that, at higher gas pressures, the temperature sinks significantly faster. Beneath a temperature of 74° C., the temperature course can be described as an approximately constant rise. With a gas pressure of 10 mbar, the temperature falls by about 0.55 K/s, and with a gas pressure of 1 mbar by 0.29 K/s. In this way, one can clearly distinguish between both gas pressure levels.

The invention claimed is:

1. An evacuated thermal insulating board having an apparatus for use in making a thermal measurement for determining the gas pressure in the evacuated thermal insulating board, the thermal insulating board having an insulating core enclosed by a covering film, the thermal measurement apparatus comprising:
   a built-in assembly between the insulating core and the covering film of the thermal insulating board, the assembly having
   (a) a body acting as a heat sink whose thermal conductivity and volume-related thermal capacity are greater than the respective values of thermal conductivity and volume-related thermal capacity of the insulating core and
   (b) a test layer placed between the heat sink and the covering film, the test layer having a thermal conductivity that varies as a function of the gas pressure within the evacuated thermal insulating board.

2. An evacuated thermal insulating board according to claim 1, wherein the thermal conductivity of the heat sink lies above 1 W/(m*K).

3. An evacuated thermal insulating board according to claim 1 or 2, wherein the thermal conductivity of the heat sink is more than 10 times as large as the thermal conductivity of the test layer at a gas pressure of less than 100 mbar.

4. An evacuated thermal insulating board according to claim 1 or 2 wherein, at or below atmospheric gas pressure, the thermal conductivity of the test layer lies below 1 W/(m*K).

5. An evacuated thermal insulating board according to claim 1 or 2 wherein the test layer comprises an open-pored material.

6. An evacuated thermal insulating board according to claim 5, wherein the test layer has a pore structure with pores of the same or larger size than pores of the insulating core.

7. An evacuated thermal insulating board according to claim 1 wherein the test layer comprises a fleece of either a polypropylene or polyester fiber, a micro fiberglass paper, a fleece of fiberglass, a thin layer of an open-pored foam material, a layer of aerogel, of diatomaceous earth, or a pressed fine powder.

8. An evacuated thermal insulating board according to claim 1 wherein the thickness of the test layer is substantially uniform, and lies in the range of from 0.05 mm to 2 mm.

9. An evacuated thermal insulating board according to claim 1 wherein the volume-related thermal capacity C of the heat sink lies between 0.5 J/(cm$^3$*K) and 5.0 J/(cm$^3$K).

10. An evacuated thermal insulating board according to claim 1 wherein the heat sink consists of aluminum, copper, iron or ceramic of high thermal conductivity.

11. An evacuated thermal insulating board according to claim 1 wherein the heat sink is a flat body with a base surface substantially parallel to the covering film or the test layer.

12. An evacuated thermal insulating board according to claim 11, wherein the thickness of the flat heat sink is substantially uniform, and measures substantially between 0.2 mm and 5 mm.

13. An evacuated thermal insulating board according to claim 11 or 12, wherein the outline of the flat heat sink is round or polygonal, wherein the diameter or the side length is between 5 mm and 300 mm.

14. An evacuated thermal insulating board according to claim 1 wherein the heat sink is a base part of a holder for getter material.

15. An evacuated thermal insulating board according to claim 1 wherein the heat sink is mounted on a flat top or bottom surface, or at a lateral surface of the thermal insulating board.

16. An evacuated thermal insulating board according to claim 1 and further comprising a sensor body with a contact surface for placing above the test apparatus from outside the evacuated thermal insulating board, the curvature of the contact surface having a curvature substantially corresponding to the curvature of the test layer beneath the enveloping film.

17. An evacuated thermal insulating board according to claim 16 wherein the sensor body is a flat body.

18. An evacuated thermal insulating board according to claim 17 wherein the sensor body has a thickness of between 0.5 mm and 50 mm.

19. An evacuated thermal insulating board according to claim 16 wherein the contact surface of the sensor body is smaller or substantially equal to that of the heat sink.

20. An evacuated thermal insulating board according to claim 16 wherein the sensor body has a thermal conductivity between 1 W/(m*K) and 1000 W/(m*K).

21. An evacuated thermal insulating board according to claim 16 wherein the sensor body comprises a metal of high thermal conductivity.

22. An evacuated thermal insulating board according to claim 16 wherein a temperature sensor is mounted on the surface or within the volume of the sensor body.

23. An evacuated thermal insulating board according to one of the claim 16 wherein a heating film is located on the surface of the sensor body.

24. An evacuated thermal insulating board according to claim 16 wherein the sensor body is at least partially enclosed by an insulating material.

25. A method for determining the gas pressure within a thermal insulating board that is enclosed by a covering film and evacuated, the method comprising:
(a) applying to the outside of the thermal insulating board, a temperature jump relative to a heat sink on a test apparatus which is situated in the evacuated thermal insulating board and covered by the enveloping film, the test apparatus comprising a heat sink and a test layer placed between the heat sink and the covering film, the test layer having a defined thermal conductivity that varies as a function of the gas pressure within the evacuated thermal insulating board whereby a heat flow, through the test layer to or from the heat sink, will be produced which is influenced by the thermal conductivity of the test layer, the heat flow being dependent on the gas pressure within the interior of the thermal insulating board; and
(b) measuring the value of this heat flow.

26. A method according to claim 25, and further comprising
(a) placing a sensor body, having a contact surface at its front, outside of and against the thermal insulating board and above the test apparatus, the curvature of the contact surface substantially corresponding to the curvature of the test layer beneath the enveloping film, and
(b) sensing said value from outside the evacuated thermal insulating board with said sensor body.

27. A method according to claim 26 wherein a heat flow is ascertained by measuring the temperature variation over time of the sensor body when the sensor body is attached to an area of the insulating board above the heat sink.

28. A method according to claim 26 wherein the sensor body temperature is regulated at a constant temperature that differs from the temperature of the heat sink.

29. A method according to claim 28, wherein the heat flow is determined through the thermal power applied to the sensor body at a temperature held constant.

30. A method according to claim 26 and further comprising mounting a heat flow meter on a contact surface of the sensor body, measuring heat flow, and holding the temperature of the sensor body constant.

31. A method according to claim 26 and further comprising enclosing the sensor body in a can-like or ring- or disc-shaped envelope and holding said envelope at substantially the same temperature as the sensor body.

32. A method according to claim 25 wherein a sensor body with a significant temperature difference relative to the test apparatus is placed onto the enveloping film.

33. A method according to claim 25, and further comprising pressing a heating film with a temperature probe onto the enveloping film above the test apparatus.

34. A method according to claim 33, and further comprising at the beginning of the measurement, switching on a heating power output in the heating film, regulating the heating power output by maintaining the temperature of the heating film constant and measuring the heat output required to maintain the temperature constant.

35. A method according to claim 33 or 34, and further comprising continually attaching the heating film with a temperature probe to the enveloping film, above the test apparatus.

36. A method according to claim 35, and further comprising covering the heating film by an insulating material.

37. A method according to claim 36, and further comprising reducing the heat loss of the heating film to the surroundings by applying sufficient heat from an additional controllable heating mechanism above the insulating material, so that its thermal power output substantially corresponds to the heat flow to the heat sink.

38. A method for the determination of the gas pressure within a thermal insulating board covered by a film and evacuated, the method comprising:
(a) applying from outside the film, a temperature jump on a test layer placed between an interior surface of the film and a heat sink within the film, the temperature jump being applied by contacting the film with a sensor board connected to a temperature probe and having a temperature different from the temperature of the heat sink, the temperature jump being relative to the heat sink, the test layer having a thermal conductivity that varies as a function of the gas pressure within the evacuated thermal insulating board so that heat flow through the test layer is a function of the gas pressure within the interior of the thermal insulating board; and
(b) measuring a value of the heat flow from outside the film through the test layer to the heat sink by recording the temperature of the sensor board at intervals of time.

* * * * *